United States Patent [19]

Dowrick

[11] 4,401,674

[45] Aug. 30, 1983

[54] INTRAMAMMARY COMPOSITIONS

[75] Inventor: John S. Dowrick, Littlehampton, England

[73] Assignee: Beecham Group Limited, United Kingdom

[21] Appl. No.: 334,437

[22] Filed: Dec. 24, 1981

Related U.S. Application Data

[63] Continuation of Ser. No. 88,858, Oct. 29, 1979, abandoned.

[30] Foreign Application Priority Data

Oct. 27, 1978 [GB] United Kingdom ............... 42337/78

[51] Int. Cl.$^3$ .............................................. A61K 31/43
[52] U.S. Cl. ................................................... 424/271
[58] Field of Search ......................................... 424/271

[56] References Cited

U.S. PATENT DOCUMENTS 4,073,920  2/1978  Dowrick ............................. 424/271

FOREIGN PATENT DOCUMENTS 2635476  2/1977  Fed. Rep. of Germany ...... 424/271

OTHER PUBLICATIONS

Chemical Abstracts, 73:48542n (1970) [Czech. Patent 132,788, Chladek, 6/15/69].
Chemical Abstracts, 74:33288f (1971) [Malkin, L. et al., Khim. Tekhnol. Topl. Masel 1970, 15(9), 22-3].
PVO International Inc., Pharmaceutical and Cosmetic Chemicals Bulletin, 1977, pp. 2-5 and Finished Product Specifications on Neobee MS, 10/9/75.

Primary Examiner—Richard A. Schwartz
Attorney, Agent, or Firm—Jacobs & Jacobs

[57] ABSTRACT

The stability of an oil intramammary formulation containing a suspension of a moisture sensitive penicillin is improved by incorporation therein of molecular sieve powder.

14 Claims, No Drawings

INTRAMAMMARY COMPOSITIONS

CROSS-REFERENCE

This is a continuation, of Ser. No. 88,858 filed Oct. 29, 1979, now abandoned.

This invention relates to intramammary compositions, to a process for their preparation, and to a method for their use.

Mummary disorders in animals are conventionally treated by the intramammary administration of suspensions or solutions of a penicillin in a suitable vehicle. It has been found that many such penicillins are unstable in aqueous vehicles and thus it is necessary to formulate them for intramammary administration in an oily vehicle to produce a product that has an acceptable shelf-life for veterinary purposes. The oily vehicles used are usually paraffin oils or vegetable oils such as arachis (peanut) oil.

With some penicillins even this formulation in an oily vehicle does not prevent at least some degradation due to moisture pick up during the shelf life of the formulation. It is an object of this invention to provide oily intramammary compositions containing such moisture sensitive penicillins, of improved stability.

Accordingly the present invention provides an intramammary composition comprising a suspension in an oily vehicle of a moisture sensitive penicillin and molecular sieve powder.

Moisture sensitive penicillins are well known to those used to working with such drugs. Penicillins for which these compositions are particularly suited include sodium amoxycillin and sodium ampicillin.

In the compositions, the active ingredient (taken as free acid) will suitably represent 0.1 to 40%, more suitably 1 to 40% (w/w). Within these ranges particularly suitable values are 4 to 8%, 15 to 25% and 30 to 40%.

Molecular sieves are commercially available in powder form. Suitable molecular sieves for our use are for example crystalline sodium, potassium or calcium alumino-silicate, preferably the calcium alumino-silicate.

The molecular sieve powder will usually be present as 0.1 to 30%, more suitably 5 to 20% of the composition, by weight.

The oily vehicle may be a mineral oil, or a vegetable oil such as arachis oil, sesame oil, corn oil, cottonseed oil, soyabean oil, olive oil, or fractionated coconut oil.

The physical properties of the composition and the release rate of active ingredient may be varied by making an appropriate choice of oily vehicle and optional additives therefore. For example when a fast milk out is required for therapy of lactating cows, then an emulsifying agent may be included in the composition to hasten the mixing of the composition with the aqueous secretions in the udder; alternatively the base described in West Germany Offenlegungsschrift No. 26 35 476 may be used, namely fractionated coconut oil (the disclosure of this Offenlegungsschrift is incorporated herein by reference). If on the other hand slow release is required for the therapy or prophylaxis of dry cows, then suitably a more hydrophobic oil vehicle which has been more strongly gelled with a gelling agent, such as aluminium stearate, is used. Thickening agents such as Thixcin R and silica may also be included in the compositions if so desired, and when present will normally represent 0.1 to 8%, more suitably 1 to 5% of the composition by weight.

We have found that preferred compositions of the invention include those comprising a suspension in fractionated coconut oil of sodium amoxycillin and molecular sieve powder; the sodium amoxycillin (as free acid) representing 5 to 30% of the composition and the molecular sieve representing 5 to 20% of the composition.

Usually it will be convenient to formulate the compositions of this invention as unit doses containing a therapeutically effective amount of the chosen active ingredient.

For example amoxycillin containing unit dose compositions suitably contain 100 to 1200 mg of amoxycillin (as free acid), for example 200 and 1000 mg.

The invention also provides a method of treatment or prophylaxis of mammary disorders in animals, which method comprises the intramammary administration of an effective amount of a composition of the invention.

For such administration, the chosen compositions will be filled into the tubes or syringe packs of the conventional type for intramammary administration, i.e. provided with a cannula nozzle for insertion into the teat to allow extrusion directly into the mammary gland via the streak canal.

A single dose of the composition will normally contain 1 to 10 gm., preferably 3 to 8 gm., of the composition.

Often a single dose of the composition of the invention will provide effective treatment or prophylaxis of the mammary disorder. However in lactating cow therapy it is common practice to repeat the dose at least once (preferably three times), each dosing taking place after milking.

The compositions of the invention may be prepared by mixing the active ingredient and the molecular sieve with the oily vehicle.

This process may suitably be carried out stepwise as follows:

(a) if a gelled or thickened base is to be used, the oil is heated, the gelling or thickening agent mixed in, and the oil then allowed to cool;

(b) the powdered active ingredient and molecular sieve is mixed into the base with stirring; and (c) high shear mixing equipment is used to produce a fine, homogeneous dispersion.

The following Examples illustrate the invention.

EXAMPLE 1

|  | gms |
| --- | --- |
| Sodium Amoxycillin | 33.3 (as free acid) |
| Thixcin R | 3.75 |
| Molecular Sieve (5Å) | 50 |
| Miglyol 812 | to 500 gms |

This composition was prepared as follows:

3.75 gms of Thixcin R were dissolved in dried Miglyol 812 by heating to about 60° C. and stirring, then allowed to cool. 50 gms of re-activated molecular sieve (calcium alumino-silicate) were incorporated by high shear stirring.

33.3 gms (free acid) of sodium amoxycillin (predried over phosphorous pentoxide) were incorporated into the base by high shear stirring. The weight of the suspension was adjusted to 500 gms by the addition of Miglyol 812.

The suspension was filled as 3 gm doses into intramammary syringes.

(Miglyol 812 has the approximate composition:

| Triglyceride of caproic acid: | 3% max. |
|---|---|
| Triglyceride of caprylic acid: | 50–65% |
| Triglyceride of capric acid: | 30–45% |
| Triglyceride of lauric acid: | 5% max. | and is available from Dynamit-Nobel U.K., Slough, Bucks, England.

Thixcin R is 12-hydroxystearin.

Molecular Sieve 5Å is commercially available from Union Carbide, and is known as calcium alumino-silicate.)

EXAMPLE 2

| | gms |
|---|---|
| Sodium Amoxycillin | 20 (as free acid) |
| Thixcin R | 2.25 |
| Molecular Sieve (5Å) | 50 |
| Miglyol 812 | to 300 gms |

This composition was prepared as follows:

2.25 gms of Thixcin R were dissolved in dried Miglyol 812 by heating to about 60° C. and stirring, then allowed to cool. 50 gms of re-activated molecular sieve (calcium alumino-silicate) were incorporated by high shear stirring.

20 gms (free acid) of sodium amoxycillin (predried over silica gel) were incorporated into the base by high shear stirring. The weight of the suspension was adjusted to 300 gms by the addition of Miglyol 812.

The suspension was filled as 3 gm doses into intramammary syringes, (dried at 50° C. for 72 hours).

EXAMPLE 3

| | gm |
|---|---|
| Sodium amoxycillin | 166.67 as free acid |
| Thixcin R | 18.75 |
| Molecular sieve (5Å) | 125.00 |
| Miglyol 812 qs to | 2500.00 |

18.75 gms of Thixcin R were incorporated into the Miglyol 812 at a temperature of 55° C. After cooling to room temperature, 125.0 gms of reactivated molecular sieve (5A) and the appropriate amount of sodium amoxycillin were incorporated using a high shear mixer. The resulting suspension was colloid milled, rehomogenised using a high shear mixer, and filled into disposable plastic syringes as 3 gm doses.

EXAMPLE 4

| | gm |
|---|---|
| Sodium amoxycillin | 500.00 as free acid |
| Thixcin R | 18.75 |
| Molecular sieve (5Å) | 125.00 |
| Miglyol 812 qs to | 2500.00 |

18.75 gms of Thixcin R were incorporated into the Miglyol 812 at a temperature of 55° C. using a high shear mixer. After cooling to room temperature 125.0 gms of reactivated molecular sieve (5A) and the appropriate amount of sodium amoxycillin were incorporated using a high shear mixer. The resulting suspension was colloid milled, rehomogenised using a high shear mixer, and filled into disposable plastic syringes as 3 gm doses.

STABILITY DATA

The stability of Example 3 was compared with a "control" batch with molecular sieve omitted.

| | With M.S. | Without M.S. |
|---|---|---|
| 2 months @ 37° C. | 99% initial | 90% initial |
| 2 months @ 50° C. | 97% initial | 79% initial |

EXAMPLE 5

| | gm |
|---|---|
| Sodium Ampicillin | 33.3 (as free acid) |
| Thixcin R | 3.75 |
| Molecular Sieve (5Å) | 50.0 |
| Miglyol 812 | to 500.0 |

3.75 g of Thixcin R were incorporated into the Miglyol at 55° C. using a high shear mixer. After cooling to room temperature, 50 g of reactivated molecular sieve (5Å) and the appropriate amount of antibiotic were incorporated by Silverson high shear mixing. The resulting suspension was filled into intramammary syringes as 3 g doses.

What we claim is:

1. A veterinary composition in intramammary administration form useful for the treatment of mammary disorders in animals which comprises a suspension in an oily veterinarily acceptable vehicle of from 0.1% to 40% by weight of a moisture sensitive penicillin calculated as free acid and from 5% to 20% by weight of calcium alumino-silicate molecular sieve powder.

2. A composition according to claim 1 wherein the amount of penicillin is 4% to 8%.

3. A composition according to claim 1 wherein the amount of penicillin is 15% to 25%.

4. A composition according to claim 1 wherein the amount of penicillin is 30% to 40%.

5. A composition according to claim 1, wherein the penicillin is sodium amoxycillin.

6. A composition according to claim 1, wherein the penicillin is sodium ampicillin.

7. A composition according to claim 1 wherein the penicillin is sodium amoxycillin which is present in the amount of from 5% to 30% and the oily vehicle is fractionated coconut oil.

8. A method of treating mammary disorders in animals which comprises the intramammary administration of a therapeutically effective amount of a suspension in an oily veterinarily acceptable vehicle of from 0.1% to 40% by weight of a moisture sensitive penicillin calculated as free acid and from 5% to 20% by weight of calcium alumino-silicate molecular sieve powder.

9. A method according to claim 8 wherein the penicillin is sodium amoxycillin.

10. A method according to claim 8 wherein the penicillin is sodium ampicillin.

11. A method according to claim 8 wherein the amount of penicillin is 4% to 8%.

12. A method according to claim 8 wherein the amount of penicillin is 15% to 25%.

13. A method according to claim 8 wherein the amount of penicillin is 30% to 40%.

14. A method according to claim 11 wherein the pencillin is sodium amoxycillin which is present in the amount of from 5% to 30% and the oily vehicle is fractionated coconut oil.

* * * * *